United States Patent [19]

Boskamp

[11] Patent Number: 5,594,337
[45] Date of Patent: Jan. 14, 1997

[54] LOCAL COIL FOR MAGNETIC RESONANCE ANGIOGRAPHY

[75] Inventor: Eddy B. Boskamp, Menomonee Falls, Wis.

[73] Assignee: Medical Advances, Inc., Milwaukee, Wis.

[21] Appl. No.: 326,556

[22] Filed: Oct. 20, 1994

Related U.S. Application Data

[63] Continuation-in-part of Ser. No. 57,939, May 7, 1993, Pat. No. 5,361,765.

[51] Int. Cl.⁶ .................................................. G01V 3/00
[52] U.S. Cl. ...................... 324/318; 324/322; 128/653.5
[58] Field of Search ................................ 324/318, 322, 324/314, 319, 307, 309, 300; 128/653.5

[56] References Cited

U.S. PATENT DOCUMENTS

| | | | |
|---|---|---|---|
| 4,825,162 | 4/1989 | Roemer et al. | 324/318 |
| 5,057,777 | 10/1991 | Kurczewski | 324/318 |
| 5,430,378 | 7/1995 | Jones | 324/318 |

*Primary Examiner*—Louis M. Arana
*Attorney, Agent, or Firm*—Quarles & Brady

[57] ABSTRACT

An angiographic coil for performing blood flow studies of the large vessels of the legs and lower pelvis employs an alternating series of coil elements having orthogonal sensitivities arrayed along a cover and base surrounding the legs and lower pelvis and supported thereby. The alternating coil pattern provides good isolation between the coils in a coil that allows easy patient positioning. In a second embodiment, structures having conductors pass between the legs when the patient's legs straddle a divider of the coil form. The coil structure is open on sides to permit easy entrance and exit from the coil by the patient. Multiple coils are used to span the length of the elongate imaging area of the legs and a pre-amplifier network is employed to limit the inductance between other coil and to provide for piecewise imaging of the entire leg and pelvis region.

22 Claims, 7 Drawing Sheets

LOCAL COIL FOR MAGNETIC RESONANCE ANGIOGRAPHY

This application is a continuation-in-part of U.S. application Ser. No. 08/057,939 filed May 7, 1993, now U.S. Pat. No. 5,361,765.

BACKGROUND OF THE INVENTION

1. Field of the Invention

The field of the invention is magnetic resonance imaging (MRI) and, in particular, local coils for use in magnetic resonance angiography (MRA).

2. Background Art

A. MRI Imaging

In MRI, a uniform magnetic field $B_0$ is applied to an imaged object along the z-axis of a Cartesian coordinate system, the origin of which is approximately centered within the imaged object. The effect of the magnetic field $B_0$ is to align the object's nuclear spins along the z-axis.

In response to a radio frequency (RF) excitation signal of the proper frequency, oriented within the x-y plane, the nuclei precess about the z-axis at their Larmor frequencies according to the following equation:

$$\omega = \gamma B_0 \qquad (1)$$

where $\omega$ is the Larmor frequency, and $\gamma$ is the gyromagnetic ratio which is a constant and a property of the particular nuclei. The component of the nuclear spins aligned with the x-y plane is termed the transverse magnetization. The rate of decay of the transverse magnetization differs for different tissues and hence may be used to distinguish among tissue in an MRI image.

Hydrogen, and in particular the nucleus (protons), because of its relative abundance in biological tissue and the properties of its nuclei, is of principle concern in such imaging. The value of the gyromagnetic ratio $\gamma$ for protons is 4.26 kHz/gauss and therefore, in a 1.5 Tesla polarizing magnetic field $B_0$, the resonant or Larmor frequency of protons is approximately 63.9 MHz.

In a typical imaging sequence for an axial slice, the RF excitation signal is centered at the Larmor frequency $\omega \pm \Delta\omega$ and applied to the imaged object at the same time as a magnetic field gradient $G_z$ is applied. The gradient field $G_z$ causes only the nuclei, in a slice with a limited width through the object along an x-y plane, to have the resonant frequency $\omega \pm \Delta\omega$ and to be excited into resonance.

After the excitation of the nuclei in this slice, magnetic field gradients are applied along the x and y axes. The gradient along the x-axis, $G_x$, causes the nuclei to precess at different frequencies depending on their position along the x-axis, that is, $G_x$ spatially encodes the precessing nuclei by frequency. The y axis gradient, $G_y$, is incremented through a series of values and encodes the y position into the rate of change of phase of the precessing nuclei as a function of gradient amplitude, a process typically referred to as phase encoding.

A weak nuclear magnetic resonance generated by the precessing nuclei may be sensed by the RF coil and recorded as an NMR signal. From this NMR signal, a slice image may be derived according to well known reconstruction techniques. An overview of NMR image reconstruction is contained in the book "Magnetic Resonance Imaging, Principles and Applications" by D. N. Kean and M. A. Smith.

2

B. Angiography

The time between the RF excitation and the recording of the NMR data may be used to detect and measure the flow of blood in blood vessels and thereby to detect obstructions and to distinguish the blood vessels from stationary tissue as demarcated by the flowing blood.

Such flow measurement may be made most simply by selectively exciting the spins in a given location and measuring the transverse magnetization of the spins at a downstream location a short while later. Examples of this "time of flight" technique are described in U.S. Pat. Nos. 3,559,044; 3,191,119; 3,419,793 and 4,777,957, hereby incorporated by reference. A variation of this technique notes the change of transverse magnetization in the region excited by the RF pulse. Examples of this method are described in U.S. Pat. Nos. 4,574,239; 4,532,474; and 4,516,582; also incorporated by reference. A third technique measures flow by making use of the fact that spins moving in a gradient magnetic field experience a phase shift. This technique is described in U.S. Pat. Nos. 4,609,872 and 5,281,916, hereby incorporated by reference.

C. Local Coils

The quality of the image produced by MRI techniques is dependent, in part, on the strength of the NMR signal received from the precessing nuclei. For this reason, it is known to use an independent RF receiving coil placed in close proximity to the region of interest of the imaged object in order to improve the strength of this received signal. Such coils are termed "local coils" or "surface coils" The smaller area of the local coil permits it to accurately focus on NMR signals from the region of interest. Further, the RF energy of the field of such a local coil is concentrated in a smaller volume giving rise to improved signal-to-noise ratio in the acquired NMR signal.

The signal-to-noise ratio of the NMR signal may be further increased by employing a coil that is sensitive to RF energy along both of a pair of mutually perpendicular axes. This technique is generally known as quadrature detection and the signals collected are termed quadrature signals.

The outputs of the quadrature coil pairs are combined so as to increase the strength of the received signal according to the simple sum of the output signals corrected for phase shift from the coils. The strength of the uncorrelated noise component of these signals, however, will increase only according to the square root of the sum of the squares of the noise components. As a result, the net signal-to-noise ratio of the combined quadrature signals increases by approximately $\sqrt{2}$ over the signal-to-noise ratio of the individual signal.

The quadrature orientation of the two coils introduces a 90° phase difference between the NMR signals detected by these coils. Therefore, combining the outputs from the two quadrature coils, to achieve the above described signal-to-noise ratio improvement, requires that one signal be shifted to have the same phase as the other signal so that the amplitudes of the signals simply add.

Such phase shifting and combining is typically accomplished by means of a hybrid network. Hybrid networks are four-port networks known in the art and having the property that when the four ports are properly terminated, energy input to two of the ports, with the proper relative phase angles, will be combined at one of the remaining two ports. The antenna coils are attached to two of the ports and the output lead is attached to a third port and produces the sum of the signals from the antenna coils, one being shifted so that they add in-phase. The remaining uncommitted port is connected to a termination resistor.

As used herein, the term quadrature coil and quadrature signal, will refer to the detecting of the NMR signal along multiple axes and combining the signals so collected, with the appropriate phase shifts to produce a signal of improved signal-to-noise ratio.

1. Volumetric Local Coils

One method of constructing a local coil is the "bird cage" construction in which two conductive loops are spaced apart along a common longitudinal axis and interconnected by a series of regularly spaced longitudinal connectors. The impedance of the loops and of the longitudinal conductors is adjusted so that the coil may be excited into resonance by a rotating transverse magnetic field at the Larmor frequency. A quadrature signal may be obtained by monitoring the current through two longitudinal conductors spaced at 90° around the periphery of the loops. Such coils are described in detail in U.S. Pat. Nos. 4,680,548, 4,692,705, 4,694,255 and 4,799,016.

The use of volumetric local coils of conventional bird cage or other quadrature design may be undesirably constraining to the patient who must be surrounded by the relatively small volume of the coil. The use of a conventional volumetric coil for angiographic imaging of the lower extremities would require threading the patient's feet through a relatively long tubular structure—a procedure that may be difficult or impossible for many patients.

SUMMARY OF THE INVENTION

The present invention provides a coil structure for imaging blood flow in the legs and lower pelvis and that provides easy access by the patient.

Specifically, the coil includes a base sized to fit against the table of an MRI machine and extending a longitudinal axis. A cover unit opposes the base and is positioned above the base to define an imaging volume between itself and the base. A number of first coils are attached to the base and the cover each having a reception pattern of a first orientation within the imaging volume. Second coils are attached to the base and cover opposed in a substantially symmetrical fashion to the first coils about the imaging volume. The second coils have at least one diametric conductor dividing each second coil into a pair of loops having a second reception pattern within the imaging volume at a second orientation substantially 90° in separation from the orientation. The first and second coils are alternated along the longitudinal axis on the base and cover.

It is a first object of the invention to provide a coil providing the advantages of a local coil while providing imaging of an entire length of a patient's lower torso and legs for angiographic diagnoses. The alternating pattern of coils with orthogonal reception patterns provides good isolation between the coils as is necessary to realize improved signal to noise ratio of a local coil.

The base and cover are fully separable And the structure of the opposed first and second coils accommodate some misalignment, permitting the base and cover to be supported and positioned by the patient.

Thus, it is another object of the invention to provide an angiographic coil that is simple in construction and that is simple to position about the patient.

The pattern of the coils may be such that a first coil is positioned above the patient's feet so that an aperture may be cut in the cover permitting the patient's toes to protrude from the cover up through the first coil when the cover is supported by the patient.

It is another object of the invention to provide a coil that may easily be positioned in close conformity to the patient.

In a second embodiment, the coil structure includes a base sized to fit against an MRI table and extending along a longitudinal axis. An upstanding divider extends vertically from the base and horizontally along the longitudinal axis and is positioned and sized to fit between and align the legs of the patient when the patient is lying on the base. An NMR receiving antenna is attached to and supported by the base and the upstanding divider.

A cover unit may be attached to the top of the upstanding divider and the NMR antenna may also be supported by the cover unit. Alternatively, a first and second upstanding flanking rail may be attached to the transverse edges of the base and the NMR antenna may also be supported by the upstanding flanking rails.

Thus, it is one object of the invention to employ the divider separating the patient's legs for coil structure and thus to eliminate the need to surround the patient with coil structures which would obstruct entrance to and exit from the coil.

The NMR antenna may include a first loop conductor supported by the cover attached to the upstanding divider and having a gap at a first side. A second loop conductor may be supported by the base and may also have a gap, the ends of the gaps of the first and second loop conductors being joined by first and second conductors passing through the upstanding divider. A third conductor passing through the upstanding divider may join the first loop conductor and the second loop conductor between points opposed to their respective gaps.

It is thus another object of the invention to provide a quadrature coil that does not surround the imaged area but that instead bisects the image area with an "I"-type structure providing for good accessibility. The loop so described has two resonant modes, one which is sensitive to a substantially vertical magnetic component and one which is sensitive to a substantially horizontal magnetic component.

Alternatively, the NMR antenna may employ a first loop conductor supported by the first upstanding flanking rail and having a gap at its bottom and a second loop conductor supported by the second upstanding flanking rail also having a gap at its bottom. A first and second conductor passing through the base joined the gaps. A third loop conductor, unconnected to the first and second loop conductors, is positioned within the divider between the first and second loop conductors.

Thus, it is another object of the invention to provide a "W"-type structure utilizing the space in between the legs of a supine patient to be open at the top and to have good sensitivity to the region of blood flow in the patient's legs.

The coil may include a co-planar shelf portion attached to one longitudinal end of the base and having a second NMR antenna supported by the shelf portion with a region of sensitivity encompassing the lower pelvis of the patient when the patient is supine on the base with the patient's legs straddling the upstanding divider. The first NMR antenna may include a plurality of reception coils spaced along the longitudinal axis. A switch alternately connects different subsets of the reception coils between an output cable to the MRI machine and isolation circuits so that a piecewise image of the entire length of the legs of the patient may be obtained.

Thus, it is another object of the invention to produce a coil having the high degree of sensitivity intrinsic to a local coil, and yet having a large imaging area suitable for angiographic imaging of the legs and lower pelvis.

Other objects and advantages besides those discussed above will be apparent to those skilled in the art from the description of the preferred embodiment of the invention which follows. Thus, in the description, reference is made to the accompanying drawings, which form a part hereof, and which illustrate one example of the invention. Such example, however, is not exhaustive of the various alternative forms of the invention. Therefore, reference should be made to the claims which follow the description for determining the full scope of the invention.

DETAILED DESCRIPTION OF THE PREFERRED EMBODIMENT

Figure 1:
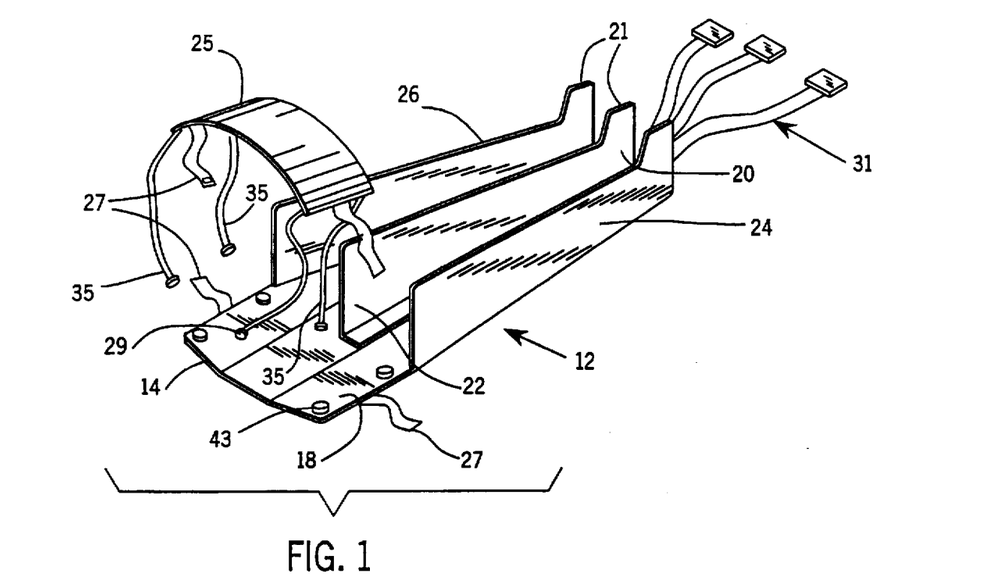
FIG. 1 is a perspective view of a first embodiment of the angiographic coil of the present invention showing the base unit with upstanding divider and upstanding flanking rails.
Figure 3:
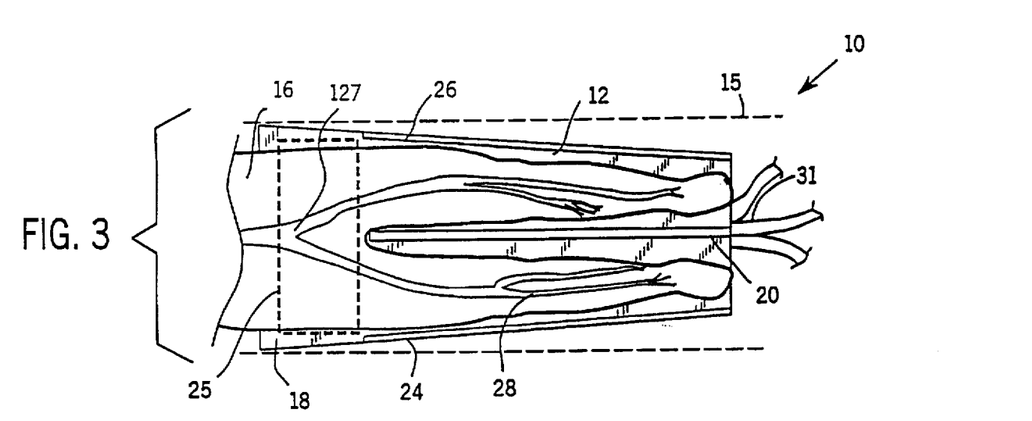
FIG. 3 is a top plan view of the coil of FIG. 1 with a patient in place showing the aortic bifurcation and the femoral arteries.

Referring to FIGS. 1 and 3, angiographic coil 10 of the present invention includes a generally planar base 12 positioned horizontally to fit on the upper surface of the table 15 of the magnetic resonance imaging machine (not shown). Curved ribs 14 are attached to the under surface of the base 12 to support the planar base 12 against the curved upper surface of the table 15. The base 12 extends transversely by the width of the table 15 and extends longitudinally by a distance suitable to support the entire length of the leg of an average patient 16 when the patient 16 is supine on the base 12 with legs extending longitudinally along the base 120 Coplanar with the base 12 and extending from one longitudinal end of the base 12 is a shelf 18 which serves to support the pelvic region of the patient 16 when the patient 16 is supine as described. The upper surface of the base 12 and shelf 18 may be covered by a thin foam cushion (not shown).

Extending upward from the base 12 along a center longitudinal axis of the base 12 is a divider 20 that fits between the legs of the patient 16 when the patient is positioned on the coil 10. The divider 20 attaches to the base 12 by fitting within a collar 22 which mechanically restrains the divider 20 from all but upward motion. The divider 20 extends upward by a height substantially equal to the vertical thickness of an average patient 16 and extends longitudinally over the entire length of the base 12 but not into the shelf 18. The patient 16, in straddling the divider 20 with legs against the divider 20, properly positions the coil 10 for imaging.

On the left and right transverse edges of the base 12 are upstanding flanking rails 24 and 26 of comparable length but of height slightly greater than the divider 20, which together with divider 20 serve to create two channels on the base 12 with transverse width suitable to receive the legs of the patient 16. Like the divider 20, the flanking rails 24 and 26 do not extend outward over the shelf 18.

Figure 4:
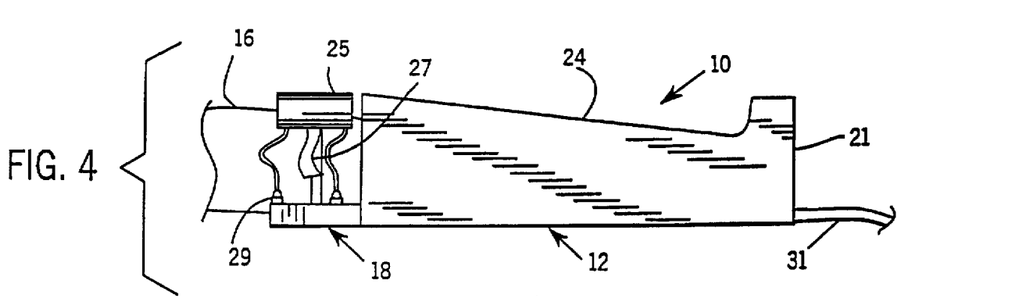
FIG. 4 is a figure similar to FIG. 3 showing a right side elevation of the coil of the present invention with the patient in place.

Referring to FIGS. 3 and 4, the divider 20 and flanking rails 24 and 26 have decreasing height, as one moves from the shelf 18 to the opposite longitudinal end of the base 12, and thus follow the decreased vertical thickness of the patient's legs when the patient 16 is positioned on the coil 10. Likewise, the base 12 tapers to be narrower as one moves from the shelf 18 toward the patient's feet reflecting the fact that the horizontal thickness of the patient's leg decreases as one moves towards the patient's feet. The tapering of the divider 20, flanking rails 24 and 26 and of the base 12 serves to bring the structure of the coil 10 closer to the patient's legs and lower pelvis which are to be imaged.

At the end of each of the divider 20 and the flanking rails 24 and 26 opposed to the shelf 18, an upward extending tab 21 increases the height of each of the divider 20 and flanking rails 24 and 26 to match in height the height of a patient's upwardly extending foot to provide support for coils (to be described) providing coverage of the patient's foot.

Referring to FIG. 3, the angiographic coil 10 is intended to provide flow images of blood moving in the large vessels 28 of the leg from the point of the aortic bifurcation 127. The flow imaging assists in detection of obstructions in these vessels which may occur at any point. For this reason, it is desirable that the area of the lower pelvis and legs be imaged.

In order to provide the high signal-to-noise ratio in such an image, small area local coils are desired. However, the length of the imaging volume is such as to prevent a single local coil of suitable size from spanning the entire region. For this reason, a series of local coils 30 (shown in FIG. 2) are employed which together span the longitudinal extent of the shelf 18 and base 12. These local coils are in two configurations depending on whether they are primarily imaging the legs or pelvic area.

Referring again to FIGS. 1 and 2, a pelvic coil 32 is supported in part by the planar area of the shelf 18 and in part by a pelvic pad 25. The pelvic pad 25 may be strapped to the anterior portion of the patient's lower pelvis by means of straps 27 and thus be held essentially parallel to the shelf 18 but in opposition to the shelf 18 about the lower pelvis of the patient 16. Straps 27 attach to counterparts affixed to the shelf 18. So positioned, the pelvic coil 32 provides sensitivity to spins above the shelf 18 in the patient's lower pelvic region.

Figure 2:
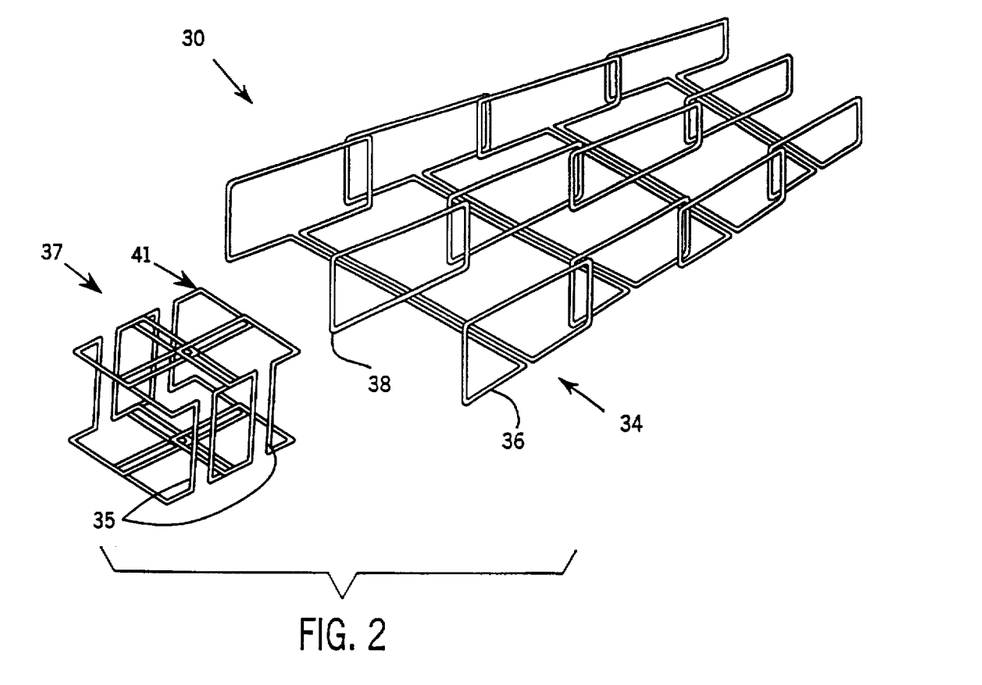
FIG. 2 is a view similar to that of FIG. 1 showing, in isolation, the overlapping leg coil elements supported within the base divider and flanking rails of FIG. 1 and a pelvic coil assembly at one end of the leg coil elements.
Figures 15, 16, 17:
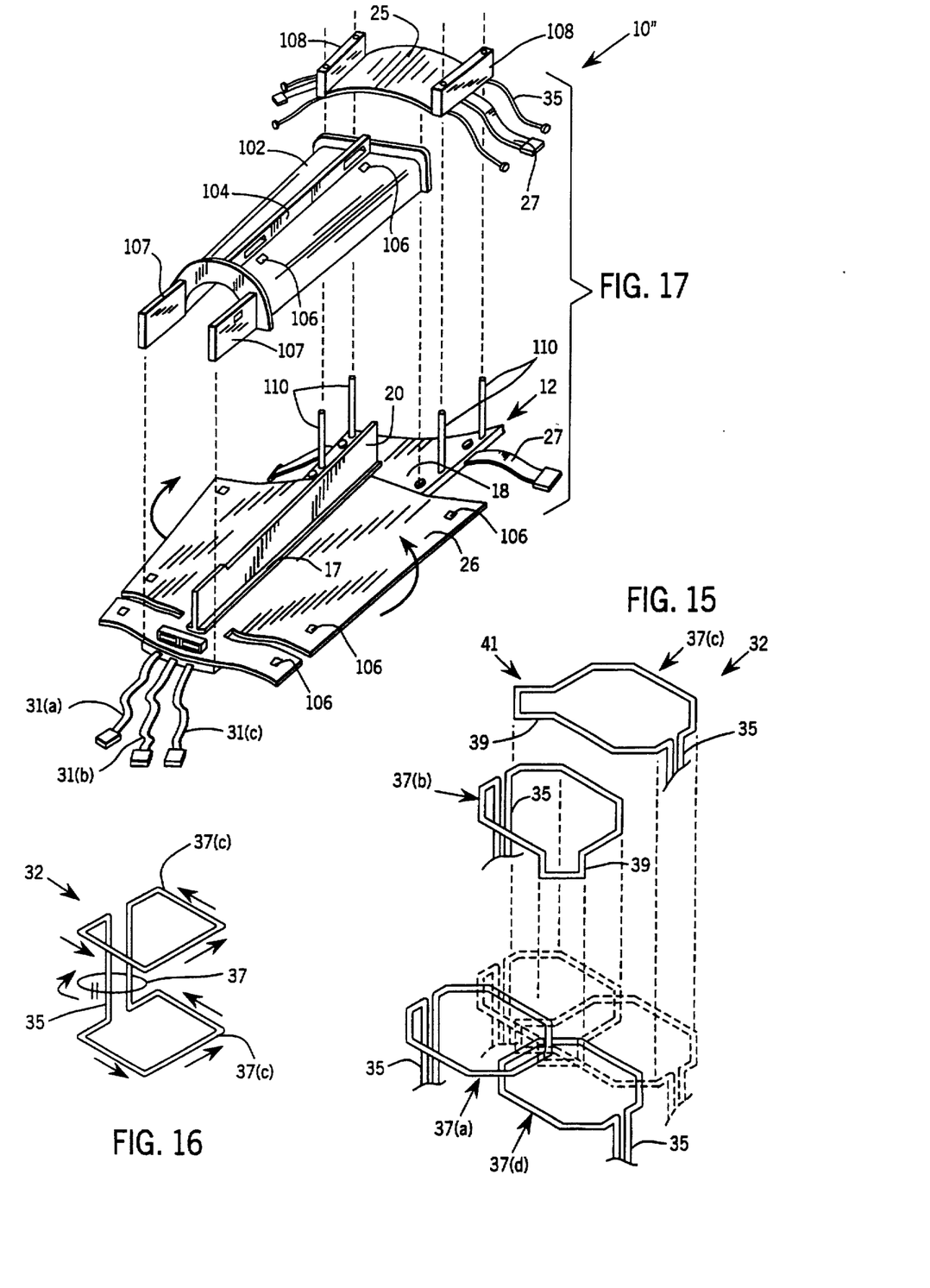
FIG. 15 is a partial exploded view of the top loops of the pelvic coil assembly of FIG. 2 showing the overlap of each top loop with its four neighbors.
FIG. 16 is a schematic representation of one coil of the pelvic coil assembly showing current flows therein.
FIG. 17 is a figure similar to that of FIG. 14 showing an alternative embodiment of the angiographic coil of FIG. 1 wherein the upstanding flanking rails are flexible and supported by a rigid but removable shell that lifts off to permit improved patient access.

Referring to FIGS. 2, 15 and 16, within each of the shelf 18 and the pelvic pad 25 is a quadripartite coil 41 comprised of four overlapping loops 37(a)–37(d) arranged in two rectilinear rows and column to cover a substantially square area. As shown in FIG. 16, corresponding vertically opposed loops 37 in the shelf 18 and pelvic pad 25 are broken at their lateral edges, toward sides of the patient as the pelvic coil 32 is positioned on the patient, to provide terminals. The terminals of a given loop 37 in the pelvic pad 25 is connected to corresponding terminals of a corresponding vertically aligned loop 37 in the shelf 18 by a co-axial cable 35. Thus, for each of the four loops 37(a)–(d) in the pelvic pad and the four opposed loops in the shelf 18 there is a co-axial cable 35. The cables 35 may be wired directly to the loops 37 in the pelvic pad 25 and connected to the coils in the shelf 18 via mating connectors 43 on the upper surface of the shelf 18.

A capacitor 37 bridges the conductors of the coaxial cables 35 at their midpoints between the shelf 18 and the pelvic pad 25 so that at resonance currents in the connected loops 37 are co-cyclic. Thus, the connected loops 37 each form a Helmholtz pair sensitive to a vertical component of the spins between the loops 37.

As described above, each loop 37 overlaps with its two neighbors within the same row or column. Thus loop 37(a) in the anatomically superior, left side of the patient overlaps with loop 37(d) to the superior, right side of the patient and also overlaps with loop 37(c) to the inferior, left side of the patient. Further, by means of tab-like sub-loops 39 on two of the loops 37((b) and 37(d), loops 37 that are diagonally opposed to each other, also overlap. Specifically, the sub-loops 39 extend the conductors of loops 37(b) and 37(c) over their diagonal neighbors.

The amount of overlap between loops 37 is such as to isolate the coils from one another by lowering their mutual inductance. A detailed description of the theory and determination of this overlap is provided in U.S. Pat. No. 5,256,971 issued Oct. 26, 1993, assigned to the assignee of the present invention and hereby incorporated by reference.

The four connected loop pairs of the pelvic coil 32 provide four signals designated as 1, 2, 3 and 4 taken across the capacitors 137 by leads (not shown).

A second group of leg coils 34 is comprised of two elements, an outer coil 36 supported by the base 12, left flanking rail 24, and right flanking rail 26; and an inner coil 38 supported by the divider 20, the inner coil bisecting the outer coil 36 and the outer coil 36 generally aligned with the transverse axis. These coil elements 36 and 38 are repeated four times over the longitudinal extent of the base 12 to provide coverage of the region of the patient's legs.

Figure 5:
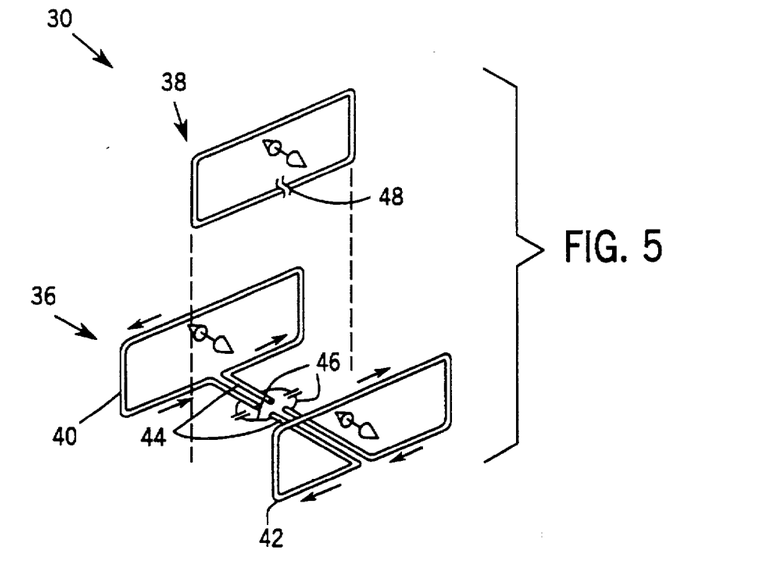
FIG. 5 is an exploded detail of one element of the overlapping coil structure shown in FIG. 2.

Each of these coils 36 and 38 overlap with the next coil longitudinally adjacent to it to eliminate mutual inductance between these adjacent coils improving the signal-to-noise ratio of a signal developed from the combination of the signals from these coils. This overlap has been discussed above with respect to the pelvic coil 32. Referring now to FIG. 5, the outer coil group 36 includes two generally rectangular loops 40 and 42, each one disposed within and aligned with respectively flanking rails 24 and 26 so that the rectangular loops lie within a vertical plane and have coincident axes of symmetry normal to those planes. Gaps cut in the lower sides of the loops 40 and 42 are joined by parallel conductors 44 passing transversely through the base 12.

Capacitors 46 are placed in series with these conductors 44 at the midpoints of these two parallel conductors 44 so as to produce a resonant mode in the coil 36 in which current flows clockwise through loop 40 when it is flowing in a counterclockwise direction in loop 42 and vice versa. The effect of this mode is that each rectangular loop 40 and 42 will be sensitive to changes in the transverse magnetization component of the NMR signal from spins near the respective loop 40 or 42. There will be no sensitivity near a plane midway between loops 40 and 42 where the equal but opposite polarity of the loops 40 and 42 will result in a cancellation of any induced current flow.

Inner loop 38 corrects for this drop in sensitivity and is thus positioned at a plane midway between the planes of loops 40 and 42 to provide for transverse sensitivity for centrally located spins.

Loops 36 and 38 at the end of the deviate base from a rectangular shape only to follow the tabs 21 of the divider 20 and the flanking rails 24 and 26 previously described (not shown in FIG. 2).

The loops 40, 42 and 38, and connecting parallel conductors 44 produce a "W"-shaped structure open at the top to allow ready access by the patient. This coil structure is possible for this particular application of angiographic imaging of a patient's legs because the region of sensitivity of the coil 10 may be physically separated by coil 38 and divider 20 as a result of the bifurcation of the legs of the patient 16.

The inner coil 38 and outer coil 36 produce two signals, one from coil 38 taken across one of the series capacitances 48 and one from coil 36 taken across a series tuning capacitor (not shown). Thus, the four pairs of coil elements 36 and 38 covering the legs of the patient produce eight signals. These eight signals together with the four signals from coil 32 and the coil of pelvic pad 25 produce twelve total signals from the angiographic coil 10. Signals from each coil 36 or 38 within the coils 30 may be assigned numbers so that signals 5 and 6 come from coils 36 and 38 in the coil group closest to the shelf 18 and successive coils 36 and 38 are given numbers 7–8, 9–10 and 11–12.

Figure 6:
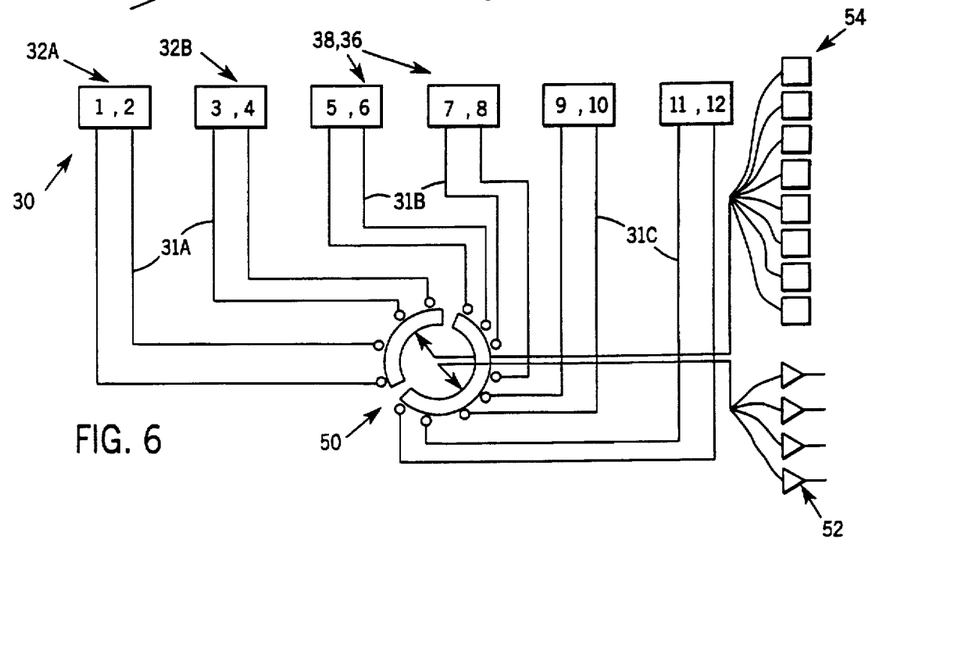
FIG. 6 is a schematic diagram of a switching system for connecting the coil elements of FIGS. 2 and 5 alternately to preamplifiers or isolation circuits to provide a piecewise image of the entire vascular structure of the lower pelvis and legs.

Referring now to FIG. 6, the total of twelve signals from the coils 30 passing over cables 31 are selectively switched by switch 50 to four preamplifiers 52 forming an input to the signal processing circuitry of a standard MRI system. To produce an image, signals 1 and 2 and 3 and 4 are received by the switch 50 and routed separately to one of the four preamplifiers 52. After completion of the data acquisition of signals 1, 2, 3 and 4, the switch 50 is moved so as to obtain data from coils 5, 6, 7 and 8.

Another image acquisition sequence is performed and the switch is again advanced to obtain the signals from coils 9, 10, 11 and 12 and forward those to preamplifiers 52. Three separate imaging sequences thus are performed to produce three images which may be combined according to methods well known in the art to provide a complete picture of blood flow within the legs and lower pelvic region of the patient 16. In the preferred embodiment, the signals received from the preamplifiers 52 are combined after image reconstruction in the MRI system.

Figure 7:
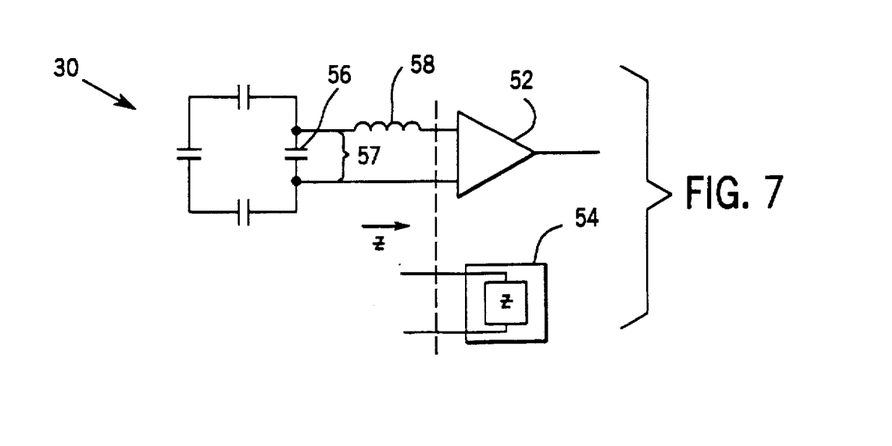
FIG. 7 is a schematic diagram of a coil element connected by a pre-amplifier or isolation circuitry according to the switch position of FIG. 6.

Switch 50 not only connects selective sets of four signals 1 through 12 to the four preamplifiers 52 but also connects those signals 1 through 12 not connected to preamplifiers 52 to dummy loads 54. Referring now to FIGS. 2 and 7, the coil groups of each coil 36 and 38 as mentioned are overlapping with their neighbors so as to reduce the mutual induction between these coil groups. This form of isolation does not address mutual inductance between every other coil group of coils 36 and 38. In order to reduce that mutual inductance, current flowing through the coils 36 and 38 of each coil group is reduced to the extent practical by employing the preamplifier 52 as part of a blocking impedance in series with the coils 36 and 38 to reduce current flow through the coil 30 and thus mutual inductance with other non-overlapping coils.

In particular, where the signal is taken across a capacitor 56, an inductance 58 is selected to be inserted in one of the conductors 57 going to the differential inputs of the preamplifier 52 so that the inductance 58 together with the impedance of the preamplifier 52 (the series combination of which shunts capacitor 56) is such as to provide parallel resonance in the loop of coil 30 blocking current flow at the NMR frequency. Generally, the magnitude of the impedance shunting capacitor 56 will be a combination of the inductance 58 and the input impedance of the preamplifier 52 as transformed by the connecting cable. Importantly, for such isolation to occur when a given coil group of 38 and 36 is not connected to a preamplifier 52, that coil group must be connected to a load 54 having a similar impedance as that of the preamplifier 52. Thus, dummy loads 54 approximating the input impedance of the preamplifiers 52 are connected to the signals not received by the preamplifiers 52.

The coil of FIG. 5 provides a high degree of sensitivity centered about the two legs of the patient when the patient straddles coil 38. The two signals produced by coils 38 and 36, however, are not in quadrature. Alternatively therefore, in a second embodiment, a quadrature coil is provided that also makes use of the ability to run coil conductors between the patient's legs.

Figure 11:
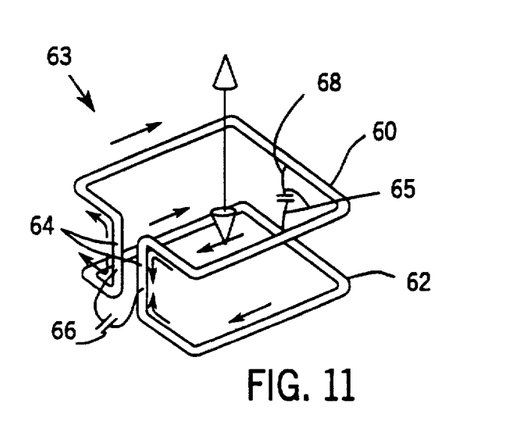
FIGS. 11 and 12 are detailed perspective views of the overlapping coil elements of FIG. 9 showing two modes of resonance which provide for quadrature detection of NMR signals in the legs.
Figure 12:
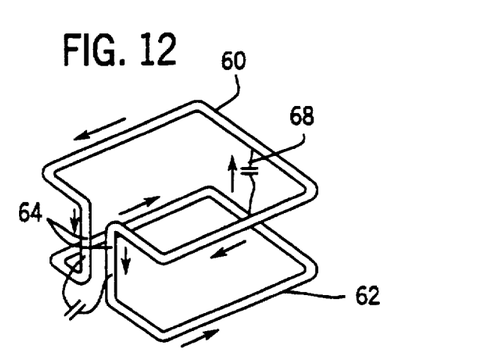

Referring now to FIGS. 11 and 12, the quadrature coil includes two generally rectangular loops 60 and 62 disposed in horizontal planes to share a common axis of symmetry normal to those planes. Gaps may be cut into corresponding transverse-running edges of the loops 60 and 62 at the midpoints of those edges to be connected by parallel, vertical conductors 64. The midpoints of the parallel conductors 64 are bridged by a capacitor 66.

Midpoints along edges of loops 60 and 62 opposite to the gaps in those loops, and thus along a longitudinal axis aligned with those gaps, are connected through conductors 65 to capacitor 68.

The resulting coil 63 operates in two resonant modes. In the first mode shown in FIG. 11, currents flowing through loops 60 and 62 and thus through capacitor 66 are co-cyclic to provide a vertical axis of sensitivity per conventional solenoid-type designs. In the second mode shown in FIG. 12, currents do not flow around loop 60 and 62 but instead flow through capacitor 68 and in the opposite direction through both of conductors 64 so as to create equal current flows in both longitudinal edges of loop 60 in a first direction and equal current flows through both longitudinal edges of loop 62 in the opposite direction. The net effect is to create an effective horizontal solenoid and thus a sensitivity to changes in magnetic flux in a horizontal transverse direction.

These first mode signals may be independently sensed across capacitor 66 whereas the second mode signals may be independently sensed across capacitor 68. Thus, the two signals from this coil across capacitors 66 and 68 provide true quadrature signals.

As before, these signals may be combined through the mechanism described with respect to FIG. 6. Again, each of the coils 63 is overlapped with its longitudinal neighbor to reduce the mutual inductance between adjacent coils 63.

Figures 8, 9:
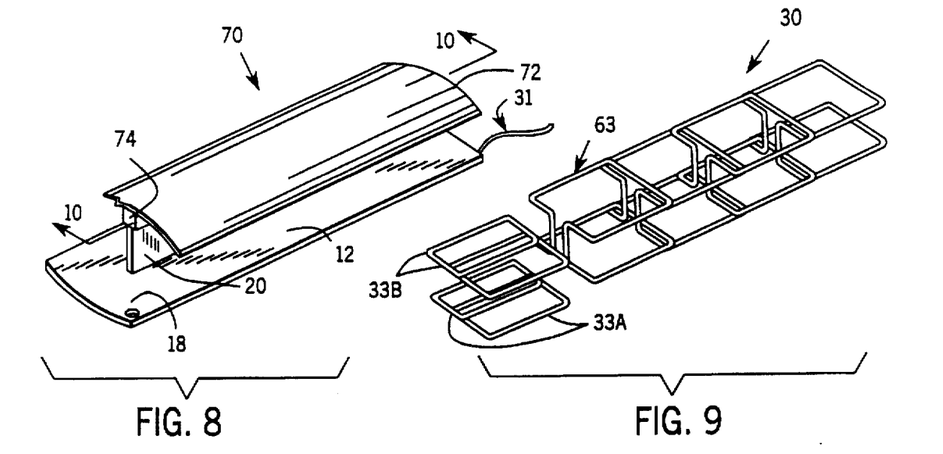
FIG. 8 is a perspective view of an alternative embodiment of the angiographic coil of the present invention having a cover portion.
FIG. 9 is a figure similar to that of FIG. 2 showing in isolation the overlapping coil elements contained in the structure of FIG. 8.

Referring now to FIGS. 8 and 11, the top loop 60 of coils 63 is supported by a cover 72 attached to the upper edge of the upstanding divider 20. The cover 72 has the same area as the base 12 and shelf 18 combined but is positioned above and parallel to the base 12 so as to support loops 60 substantially parallel to loops 62 that are contained in the base 12. The vertical conductors 64 and conductors 65 pass through the divider 20.

In the embodiment of FIG. 8, the base 12 is concave upward in the transverse direction and the cover 72 is concave downward so as to bring the loops 60 and 62 into closer proximity with the legs of the patient 16 (not shown in FIG. 8). As before, the base 12 and cover 72 taper to become more narrow toward the patient's feet and the divider 20 tapers downward to provide closer coupling by the coils to the patient. Generally, the loops 60 and 62 change in transverse width to conform with the tapering cover 72 and base 12.

Figure 10:
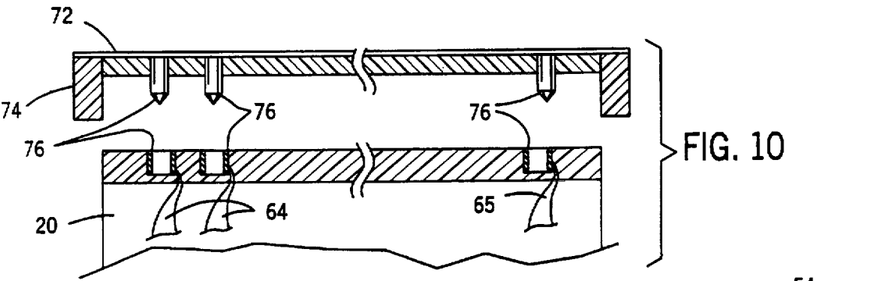
FIG. 10 is a cross-section along lines 10—10 of FIG. 8 showing a joint permitting removal of the cover portion from the upstanding divider of the coil of FIG. 8.

Referring to FIGS. 10 and 8, to facilitate positioning the patient into the coil 70, the cover 72 may be attached to the upstanding divider 20 by means of a collar 74 similar to collar 22 previously described in that it allows detachment of the cover 72 from the upstanding divider 20. Whereas divider 20 in coil 10 of FIG. 1 is electrically separate from the base 12, this is not true in the embodiment of FIG. 8 and electrical connectors 76 are provided to connect and disconnect parallel conductors 64 and conductors 65 to capacitor 68 between the upper loop 60 contained in the cover 72 and the lower loop 62 contained in the base 12 when the cover 72 is replaced or removed.

The conductors 64 and the leads connecting capacitor 68 may be copper foil affixed to the surfaces of the respective elements of the coil 10.

Referring now to FIGS. 8 and 9, the coils of FIGS. 11 and 12 are augmented by a coil on the shelf 18 and within the cover 72 above the shelf to image the pelvic region. This coil may be the pelvic coil 32 previously described or may be a coil 33 (serving a similar function to pelvic coil 32 previously described) consisting of a pair of coils 33A and 33B each having two overlapping rectangular loops generally conforming to and supported by the planar area of the shelf 18 or the cover 72, respectively, and having separate leads for transmitting their received signals. The sides of the loops are generally parallel to the adjacent edges of the shelf 18, each loop of coil 33A or 33B occupying only slightly more than half the area of the shelf 18 or corresponding area of the cover 72 so as to overlap along the central longitudinal axis of the shelf 18 or cover 72. Coils 33 provides coverage of NMR signals in the region of the patient's lower pelvis. The signals 1 and 2 are taken across one of the capacitances that tune the loops of coil 33A into resonance. The signals 3 and 4 are taken across one of the capacitances that tune the loops of coil 33B into resonance.

Figures 13, 14:
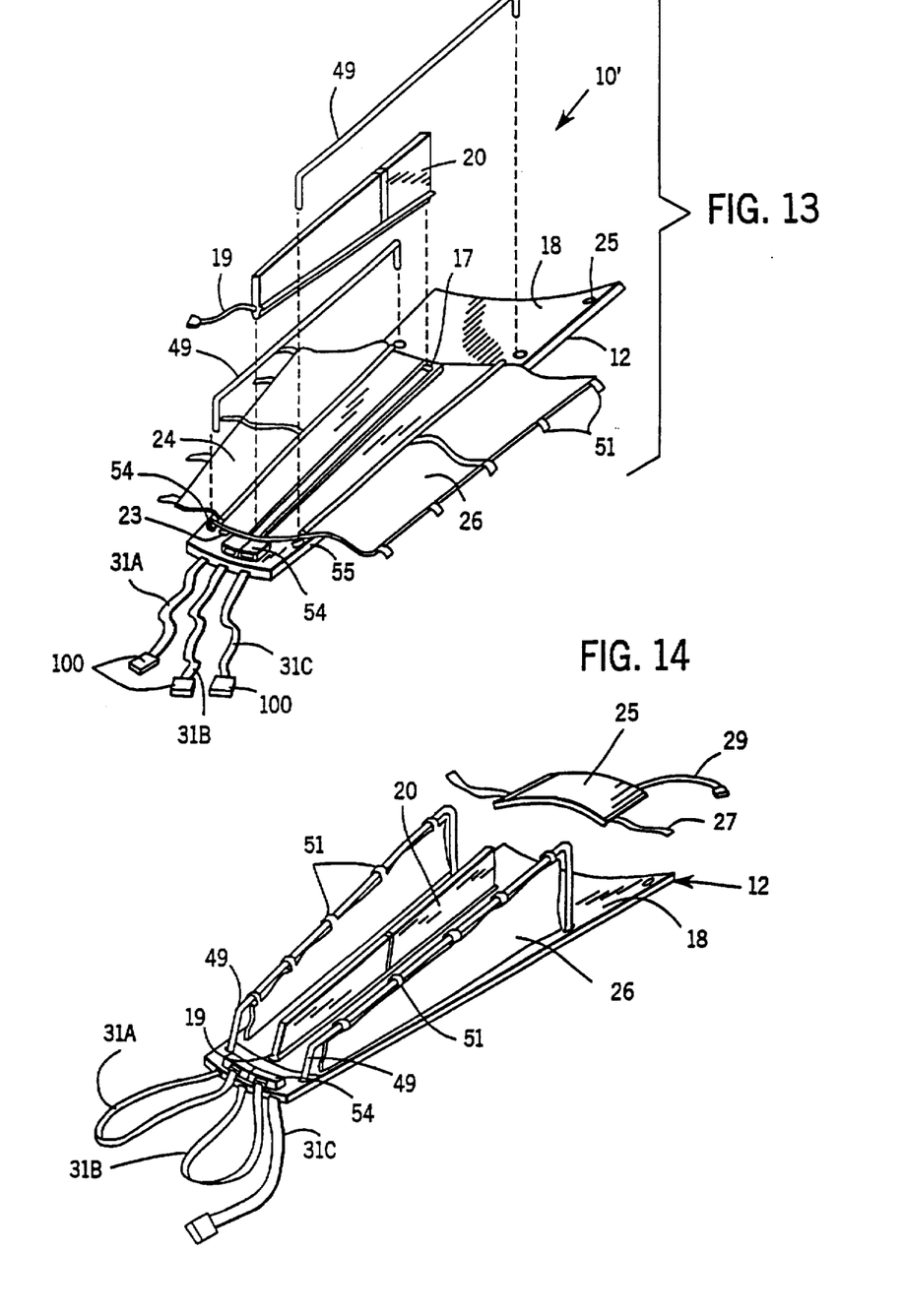
FIGS. 13 and 14 are exploded and assembled perspective views of an alternative embodiment of the angiographic coil of FIG. 1 wherein the upstanding flanking rails are flexible and supported by rigid but removable support poles that fold to permit improved patient access.

Referring now to FIGS. 13 and 14 in another embodiment 10', the coil of FIGS. 1 and 2 may be provided with improved access by constructing the left and right flanking rails 26 and 24 from a continuous sheet of flexible printed circuit board. The use of flexible printed circuit board provides that the coils 36 supported by the base 12 and the side rails 26 and 24 may be unfolded into a generally planar configuration for easy access of the coil 10' by a patient. To further improve this access, coil 38 contained in divider 20 may be removable from the base 12 by lifting the divider 20 from a channel 17 affixed along the midline of the upper surface of the base 12. Electrical connections to the coils 38 contained in the divider 20 may be provided through a flexible conductor 19 that may be disconnected from a mating receptacle 23 on the upper surface of the base 12.

After the patient 16 is positioned supine on the upper surface of the base 12 with legs straddling the channel 17, the divider 20 may be inserted into the channel 17 and conductor 19 plugged into receptacle 23. Left and right upstanding rails 26 and 24 may then be folded upward to a vertical position against the patient's legs as shown in FIG. 14. U-shaped supporting rails 49 may then be inserted into sockets 55 in the upper surface of the base 12 to provide a frame to support the upstanding rails 26 and 24. The upstanding rails 26 and 24 are held to a horizontally extending portion of the rails 49 by means of flexible tabs 51 extending out from the upper edge of the rails 26 and 24 to wrap around the rails 49 and attach to themselves by means of Velcro.

The pelvic pad 25 may be attached to the patient as previously described. The pelvic coil 33 may use a single cable 29 connected to the base 12 to provide a path for the signals 1 and 2 of the coil of pelvic pad 25. The collected signals from the various coils in the coil 10' are provided at three cables 31(a) through 31(c). Cable 31(a) carries the conductors for signals 1, 2, 3 and 4; 31(b) carries the conductors for signals 5, 6, 7 and 8; and cable 31(c) carries the conductors for signals 9, 10, 11 and 12. Each cable 31 terminates in a connector 100.

During imaging, a connector 100 for one of the cables 31(a) through 31(c) is connected to the MRI machine (not shown) and the other two cables 31 are connected to terminator blocks providing dummy loads 54 attached to the upper surface of the base 12 near the patient's feet to provide the termination function previously described.

Referring now to FIG. 17 in yet another embodiment 10", the continuous sheet of flexible printed circuit board from which the left and right flanking rails 26 and 24 are constructed may be supported by a rigid but non-conducting shell 102 which may be placed atop the base 12 to cover the patient's legs when the patient is supine on the base 12. The shell 102, which may be advantageously formed from a single piece of thermoplastic material, has a transverse cross section that is generally an inverted "U" so that it may be placed over the patient after the patient is in position on the base 12. The shell 102 is aligned and secured by guide pegs and holes (not shown) in the shell and base, respectively.

A longitudinal rib 104 running along the upper side of the shell 102 incorporates handgrip holes to aid in the placing of the shell 102 over the patient. Once in place, the flexible material of the left and right flanking rails 26 and 24 is laid across the shell and secured by Velcro tabs 106. The foot end of the shell 102 is open upward to accommodate upward extension of the patient's feet and has upwardly extending walls 107 to which the lower portion of the left and right flanking rails 26 and 24 may be attached to flank the patient's feet.

The shell 102 permits the spatial location of the left and right flanking rails 26 and 24 to be accurately placed and well defined when the latter rails are made of a flexible material. The shell 102 further allows the left and right flanking rails 26 and 24 to follow a more complex, curved surface as defined by the shell 102.

Again, the divider 20 may be removable from the base 12 by lifting the divider 20 from a channel 17 affixed along the midline of the upper surface of the base 12.

The pelvic coil of this embodiment 10" employs the coils previously described with respect to FIGS. 2, 15 and 16 and thus requires four coaxial cables 35. The pelvic pad 25 includes at its lateral edges rod guides 108 having vertically extending holes for receiving rods 110 extending upwardly from the base 12 which serve to better align the pelvic pad 25, and hence its contained coil, with the corresponding coil in the shelf 18. Generally, the rods 110 pass through each of four corners of the pelvic pad 25 keeping it from tipping with respect to the base 12 and centering it over the base 12.

As is well known in the art, each loop of the above described coils is broken at regular intervals around its circumference by capacitances (not shown) so that the combined series inductance of the conductors of the coils and capacitance so inserted makes the coils resonant at the NMR frequency for the given magnetic resonance imaging system.

Each coil also includes passive decoupling (not shown) as is well known in the art, which decouples the loop from the initial high energy RF excitation field but allows it to couple to the subsequent lower NMR signal to be detected. Examples of the detailed electrical structure of such loops including passive decoupling networks suitable for use with the present invention are described in U.S. Pat. No. 5,136,244 issued Aug. 4, 1992, assigned to the same assignee as the present invention and hereby incorporated by reference.

Figure 18:
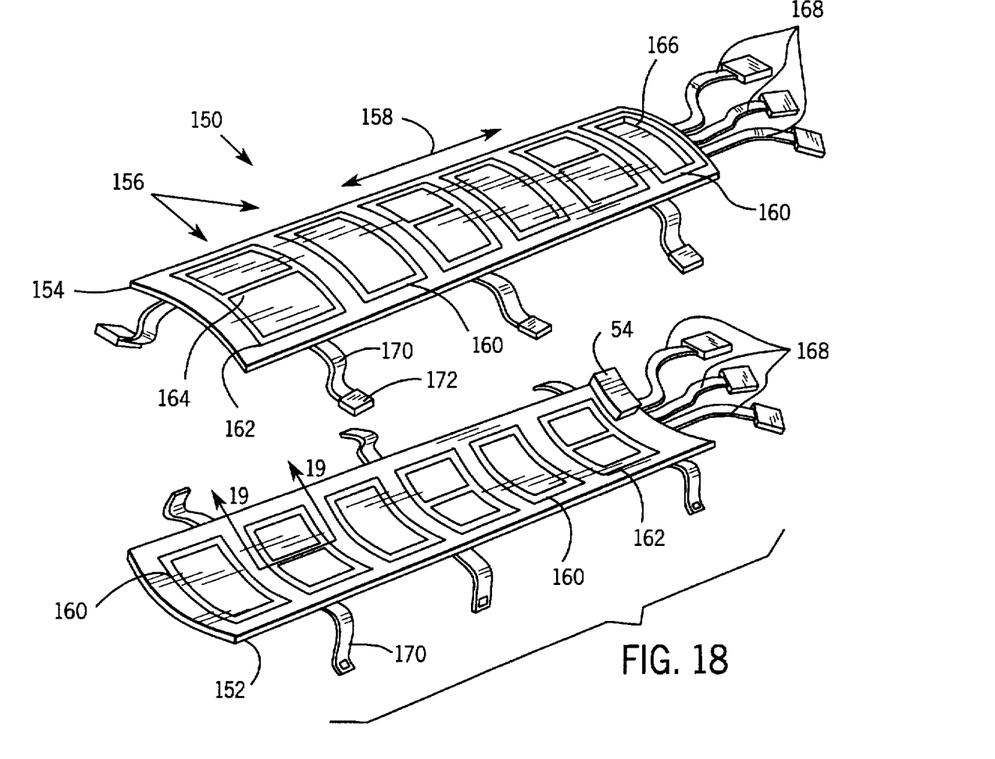
FIG. 18 is a figure similar to that of FIGS. 1 and 8 showing an embodiment of the invention employing a patient supported cover and base.

Referring now to FIG. 18, in another embodiment of the angiographic coil 150, the coils are supported on a semi-cylindrical base 152 and semi-cylindrical cover 154 having concave inner surfaces receiving, respectively, the posterior and anterior surfaces of the lower pelvis and legs of the patient 16 (not shown). The lower surface of the base 152 generally conforms to the upper surface of the MRI table to provide a rigid support for the base 152.

The base 152 and cover 154 are constructed of a nonconductive plastic material to provide support for a number of coils 156 attached to the surface of the base 152 and cover 154, the coils 156 being spaced along the longitudinal axis 158 of each of the base 152 and cover 154. The coils 156 are of two types, a first single loop coil 160 and a second two loop coil 162.

The single loop coil 160 may be generally rectangular in shape to align with the edges of the base 152 and cover 154, and may be constructed of copper foil or the like adhered directly to the surface of the base 152 and cover 154. As with all coils described in this application, the conductors of the single loop coil 160 are broken at regular intervals by capacitances so as to tune the loop into resonance at the Larmor frequency. The single loop coil 160 also includes a decoupling circuit (not shown) to isolate the loop from the high energy RF excitation pulse as is well known in the art.

The two loop coil 162 may also be generally rectangular in outside dimension but is bifurcated by a single conductor 164 extending longitudinally across the center of the coil 162 to produce two loops having a shared wall of that conductor 164. Coil 162 is tuned, at resonance, to a mode having counter-rotating currents in each of the two loops such currents adding in the center conductor 164 where the coils signal is obtained.

In the preferred embodiment, six single loop coils 160 and six two loop coils 162 are used. Three of each are positioned on the cover 154 and three on the base 152, with the single loop coil 160 alternating with the two loop coils 162 as one progresses longitudinally along either of the base 152 and cover 154. Accordingly, when base 152 and cover 154 are aligned with each other about the patient, a two loop coil 162 is symmetrically opposed with a single loop coil 160 about the volume between the base 152 and the cover 154 and hence about the patient. Thus, starting at the superior edge of the cover 154 one encounters a two loop coil 162, a single loop coil 160, a two loop coil 162, a single loop coil 160, a two loop coil 162, then a single loop coil 160, the latter being at the inferior edge of the cover 154.

Cut within the area of the single loop coil 160 at the inferior edge of the cover 154 is an aperture 166 sized to admit the patient's toes when the cover 154 is placed upon the supine patient's lower torso and legs. The aperture 166 thus allows the cover 154 to closely conform to the legs of the patient.

In contrast starting at the superior edge of base 152 there is a single loop coil 160, a two loop coil 162, a single loop coil 160, a two loop coil 162, a single loop coil 160 ending in a two loop coil 162. In this manner a single loop coil 160 is always opposite a two loop coil 162 and vice versa.

Signals are developed from each of these coils 160 and 162 independently. For the single loop coils 160 the signal is taken across one of the capacitors (not shown) tuning the single loop coil 160 at its periphery. For the two loop coil 162 the signal is taken across a capacitor (not shown) in the bifurcating conductor 164.

These signals are carried by cables 168 similar to cables 31 as have been previously described to the MRI equipment, however the conductors 168 carry half the number of signals as the cables 31 by virtue of the electrical independence of the cover 154 and base 152. Terminating blocks 54 are attached to both the cover 154 and base 152 so that those cables 168 not being used to carry signals to the MRI machine may be properly terminated as described above with respect to FIGS. 6 and 7.

Figure 19:
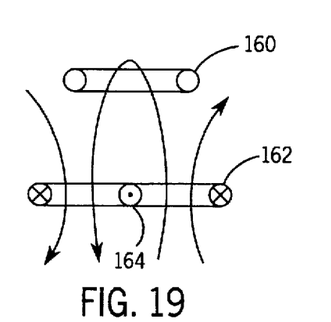
FIGS. 19 and 20 are cross sections of the coils positioned on the cover and base of FIG. 18 as taken along line 19—19 showing the magnetic flux generated by each coil at resonance and the intrinsic isolation of the opposed coils.
Figure 20:
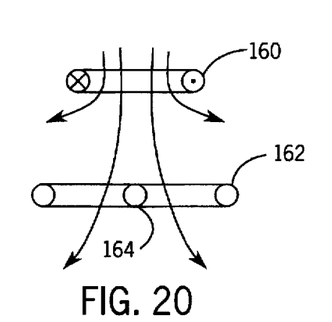

Referring now to FIGS. 19 and 20, coils 160 and 162 which are placed in opposed configuration on the base 152 and the cover 154, are sensitive to the NMR signal along different axes. Specifically, coils 160 are generally sensitive to magnetic flux along a vertical axis perpendicular to the longitudinal axis 158 whereas the two loop coil 162 is generally sensitive to magnetic flux along the longitudinal axis 158. As a result, coils 160 and 162 when opposed to each other on the base 152 and cover 154, are isolated with respect to mutual inductance and provide signals, which when combined, produce a signal-to-noise improvement over either coil 160 or 164 alone. As shown in FIG. 19, magnetic flux generated by countervailing currents in two loop coil 162 pass symmetrically in both directions through opposed coil 160 generating no net current flow. Likewise, flux generated by a circulating current in single loop coil 160, shown in FIG. 20, produces similar fluxes in the two loops of dual loop coil 162 thereby also generating no net current flow in the center conductor 164.

Figure 21:
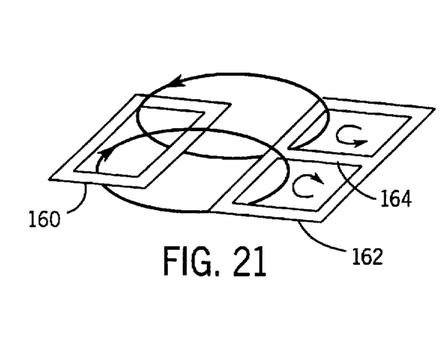
FIGS. 21 and 22 are perspective views of two adjacent coils on either of the cover or base of FIG. 18 showing the magnetic flux generated by each coil at resonance and the intrinsic isolation of the adjacent coils.
Figure 22:
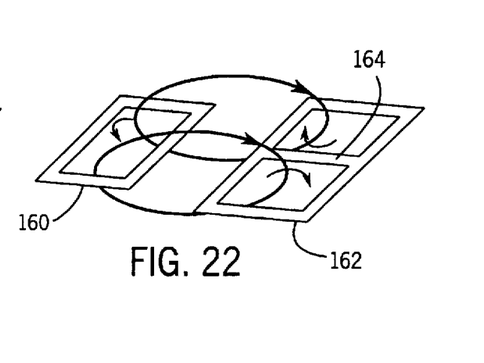

Referring to FIGS. 21 and 22 similarly, coils 160 and 162 that are adjacent on the cover 154 or base 152, rather than opposed across the imaging volume, are likewise isolated. The countervailing currents of the two loop coil 162 generating opposing fluxes through the adjacent coil 162 which when superimposed produce no net current flow in coil 160 as shown in FIG. 21. Similarly, as shown in FIG. 22, the flux generated by coil 160 induces co-cyclic currents in the two loops of coil 162 producing no net current flow in bifurcating conductor 164 across which the signal is detected.

Thus, immediately opposed and immediately adjacent coils are isolated by virtue of the difference in sensitivity axes of those coils and the alternating use of the first and second coil types 160 and 162. There will be some coupling between coils of similar types disposed diagonally across the imaging volume and this residual coupling is handled by the decoupling circuit described above with respect to FIG. 7.

Coils suitable for use with this embodiment are described in detail in the parent application Ser. No. 08/057,939 filed May 7, 1993 and entitled *Two Part Quadrature NMR Coil*, assigned to the assignee of this application and hereby incorporated by reference.

Straps 170 may be attached to the left and right edges of the base 152 and cover 154 to permit the base 152 and cover 154 to be drawn together against the patient, the straps connected through buckles 172. The concave surface of the base 152 and cover 154 help align the base 152 and cover 154 with the patient. Foam pads (not shown) may be placed between the patient and the base 152 and cover 154 to improve this alignment and to provide a more comfortable surface against which the patient is in contact.

The Applicant has determined this coil design accommodates some degree of misalignment between the coils before coupling between opposed coils, thus making possible the floating structure of the base 152 and cover 154 which provides superior access by the patient. In operation, the coil form may be assembled after the patient is in position on the table.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

I claim:

1. An MRI coil for angiographic imaging of the lower trunk and legs comprising:

a base sized to fit against a table of an MRI machine and extending along a longitudinal axis;

a cover unit opposing the base and positionable above the base, together with the base to define an imaging volume therebetween;

a plurality of first coils attached to the base and cover and having first reception patterns which couple to RF magnetic fields of a first orientation within the imaging volume to produce first signals; and a plurality of second coils attached to the base and cover and opposed substantially symmetrically to the first coils about the imaging volume, the second coils having at least one diametric conductor to divide each second coil into a pair of loops, the second coils having second reception patterns which couple to RF magnetic fields of a second orientation within the imaging volume to produce second signals, the second orientation having an angular separation from the first orientation of substantially 90 degrees;

wherein the first and second coils are alternated along the longitudinal axis.

2. The MRI coil of claim 1 wherein the cover includes an aperture located on the cover at a position above a patient's feet when the patient's lower trunk and legs are positioned within the imaging volume and wherein the first coil is a single loop surrounding the aperture permitting toes of the patient's feet to extend through the aperture.

3. The MRI coil of claim 1 wherein base and cover are cylindrically concave about the imaging volume.

4. The MRI coil of claim 1 wherein the cover and base are sized so as to be self-supporting against the patient and including flexible straps attached to at least one of the cover and base to draw the cover and base toward each other about the patient.

5. An MRI coil for angiographic imaging of the lower trunk and legs compromising:

a base sized to fit against a table of an MRI machine and extending along a longitudinal axis;

an upstanding divider extending vertically from the base and horizontally along the longitudinal axis, the divider being sized so as to fit between and align the legs of a supine patient lying on the base;

an NMR receiving antenna having a region of sensitivity encompassing both legs of the patient when the patient is supine on the base with the patient's legs straddling the upstanding divider;

a cover unit attached to the top of the upstanding divider to oppose the base and wherein the NMR antenna is supported by the base, the upstanding divider, and cover unit; and wherein the upstanding divider detaches from one of the base and cover and wherein the NMR antenna includes electrical connectors to permit separation of the portions of the NMR antenna supported by the cover from the portions supported by the base to permit separation of the base and cover for ingress and egress by the patient.

6. The MRI coil of claim 5 wherein the NMR antenna comprises:

a first loop conductor supported by the cover having four sides, the first loop conductor having a first gap at the first side, the ends of the loop at the gap forming a first and second terminal;

a second loop conductor supported by the base and opposed to the first loop conductor about an imaging volume, the second loop conductor having a second gap at the first side, the ends of the second loop at the gap forming a third and fourth terminal;

a first conductor supported by the divider joining the first terminal to the third terminal;

a second conductor supported by the divider joining the second terminal to the third terminal;

a third conductor supported by the divider joining the first loop conductor at a point diametrically opposed to the first gap, to the second loop conductor at a point diametrically opposed to the second gap;

wherein in a first resonant mode current flows in the same direction in the second sides of the first and second coils and current flows in the same direction in the fourth sides of the first and second coils to be sensitive to changing magnetic vector along a substantially vertical axis; and wherein, in a second resonant mode, current flows in the opposite direction in the second sides of the first and second coils and current flows in the opposite direction in the fourth sides of the first and second coils to be sensitive to changing magnetic vector along a substantially horizontal axis.

7. The MRI coil of claim 5 including a coplanar shelf portion is attached to one longitudinal end of the base and including a second NMR antenna supported by the shelf portion to have a region of sensitivity encompassing the lower pelvis of the patient when the patient is supine on the base with the patient's legs straddling the upstanding divider.

8. The MRI coil of claim 7 including a third NMR antenna positioned opposite the second NMR antenna about the lower pelvis of the patient when the patient is supine on the base with the patient's legs straddling the upstanding divider.

9. The MRI coil of claim 5 wherein the NMR antenna includes a plurality of reception coils spaced along the longitudinal axis and including a switch alternately connecting different subsets of the reception coils between an output cable so that a piecewise image of the entire length of the legs of a patient may be obtained for a patient supine on the base with the patient's legs straddling the upstanding divider.

10. An MRI coil for angiographic imaging of the lower trunk and legs comprising:

a base sized to fit against a table of an MRI machine and extending along a longitudinal axis;

an upstanding divider extending vertically from the base and horizontally along the longitudinal axis, the divider being sized so as to fit between and align the legs of a supine patient lying on the base;

an NMR receiving antenna supported by the base and divider to have a region of sensitivity encompassing both legs of a patient when a patient is supine on the base with the patients legs straddling the upstanding divider; and first and second upstanding flanking rails attached to transverse edges of the central portion of the base wherein the NMR antenna is supported by the base, the upstanding divider and the first and second upstanding flanking rails.

11. The MRI coil of claim 10 wherein the first and second upstanding flanking rails are attached to the transverse edges of the base by hinges having longitudinal hinge axes so that the first and second upstanding flanking rails may be folded horizontally outward for patient axes and wherein the NMR antenna includes flexible conductor portions to permit flexure of the NMR antenna as it passes between the base and the first and second upstanding flanking rails to permit easy access by a patient.

12. The MRI coil of claim 10 wherein the first and second upstanding flanking rails are constructed of flexible material and where the NMR antenna as supported by the first and second upstanding rails is flexible so that the first and second upstanding flanking rails may be folded horizontally outward for patient access and including rigid support poles that may be inserted and removed from the base to hold the first and second flanking rails in an upstanding position when inserted in the base.

13. The MRI coil of claim 10 wherein the first and second upstanding flanking rails are constructed of flexible material and where the NMR antenna as supported by the first and second upstanding rails is flexible so that the first and second upstanding flanking rails may be folded horizontally outward for patient access and including rigid support shell that may be placed over the patient on the base to hold the first and second flanking rails in a predetermined configuration when the first and second flanking rails are folded against the shell.

14. The MRI coil of claim 10 wherein the NMR antenna comprises:

a first loop conductor supported by the first upstanding flanking rail and having four sides, the first loop conductor having a first gap at the first side, the ends of the loop at the gap forming a first and second terminal;

a second loop conductor supported by the second upstanding flanking rail opposed to the first loop conductor about an imaging volume, the second loop conductor having a second gap at the first side, the ends of the second loop at the gap forming a third and fourth terminal;

a first conductor supported by the base joining the first terminal to the third terminal;

a second conductor supported by the base joining the second terminal to the third terminal; and a third loop conductor supported by the upstanding divider and positioned between the first and second loop conductors in opposition to the first and second loop conductors to bifurcate the imaging volume;

wherein in the first and second loops have a resonant mode sensitive to changing magnetic vector along a substantially vertical axis; and wherein the third loop conductor has a resonant mode sensitive to a changing magnetic vector along a substantially horizontal axis.

15. An MRI quadrature coil comprising:

a first loop conductor having consecutive, first, second, third and fourth sides the first loop conductor having a first gap at the first side, the ends of the loop at the gap forming a first and second terminal;

a second loop conductor opposed to the first loop conductor about an imaging volume also having consecutive first, second, third and fourth sides, the second loop conductor having a second gap at the first side, the ends of the second gap forming a third and a fourth terminal;

a first conductor joining the first terminal to the third terminal;

a second conductor joining the second terminal to the fourth terminal;

a third conductor joining the first loop conductor at a point diametrically opposed to the first gap, to the second loop conductor at a point diametrically opposed to the second gap;

wherein, in a first resonant mode, current flows in the same direction in the second sides of the first and second coils and current flows in the same direction in the fourth sides of the first and second coils to be sensitive to changing magnetic vector along a first axis; and wherein, in a second resonant mode, current flows in the opposite direction in the second sides of the first and second coils and current flows in the opposite direction in the fourth sides of the first and second coils to be sensitive to changing magnetic vector along a second axis substantially perpendicular to the first axis.

16. The MRI quadrature coil of claim 15 including a first capacitor joining the midpoints of the first and second conductors across which a signal indicating the changing magnetic vector along the first axis may be developed and including a second capacitor breaking the midpoint of the third conductor across which a signal indicating the changing magnetic vector along the second axis may be developed.

17. The MRI quadrature coil of claim 15 wherein the first and second loop are substantially planar and rectangular and wherein the first, second and third conductors are normal to the planes of the first and second loops.

18. An MRI quadrature coil comprising:

a first loop conductor having consecutive first, second, third and fourth sides, the first loop conductor having a first gap at the first side, the ends of the loop at the gap forming a first and second terminal;

a second loop conductor opposed to the first loop conductor about an imaging volume also having consecutive first, second, third and fourth sides, the second loop conductor having a second gap at the first side, the ends of the second loop at the gap forming a third and fourth terminal;

a first conductor joining the first terminal to the third terminal;

a second conductor joining the second terminal to the fourth terminal; and a third loop conductor positioned between the first and second loop conductors in opposition to the first and second loop conductors to bifurcate the imaging volume;

wherein the first and second loops have a resonant mode sensitive to changing magnetic vector along a first axis; and wherein the third loop conductor has a resonant mode sensitive to a changing magnetic vector along a second axis substantially perpendicular to the first axis.

19. The MRI quadrature coil of claim 18 including a first capacitor joining the midpoints of the first and second conductors across which a signal indicating the changing magnetic vector along the first axis may be developed and including a second capacitor breaking the third loop conductor across which a signal indicating the changing magnetic vector along the second axis may be developed.

20. The MRI quadrature coil of claim 18 wherein the first, second and third loops are planar and rectangular and parallel to each other.

21. A surface coil having four conductive loops arranged on an open surface so that each of the conductive loops overlaps with all three of the other conductive loops, the overlapping being of an amount to eliminate mutual inductance between the loops.

22. The surface coil of claim 20 including a second four conductive loops, each of the second four conductive loops aligned with one of the first four conductive loops along axes through the respective loops, and further including conductors connecting aligned pairs of the loops so that at a resonant frequency current flows co-cyclically in the loops of each aligned pair.

* * * * *